(12) United States Patent
Klapproth et al.

(10) Patent No.: US 7,433,738 B2
(45) Date of Patent: Oct. 7, 2008

(54) DEVICE FOR MUSCLE STIMULATION

(75) Inventors: Peter Klapproth, Lübeck (DE); Eckart Ulbrich, Timmendorfer Strand (DE)

(73) Assignee: Fides Finanz-Invest GmbH & Co. KG, Timmendorfer Strand (DE)

( * ) Notice: Subject to any disclaimer, the term of this patent is extended or adjusted under 35 U.S.C. 154(b) by 159 days.

(21) Appl. No.: 10/568,601

(22) PCT Filed: Sep. 3, 2004

(86) PCT No.: PCT/DE2004/001970

§ 371 (c)(1),
(2), (4) Date: Feb. 14, 2006

(87) PCT Pub. No.: WO2005/023363

PCT Pub. Date: Mar. 17, 2005

(65) Prior Publication Data

US 2006/0276855 A1    Dec. 7, 2006

(30) Foreign Application Priority Data

Sep. 3, 2003   (DE) ................................. 103 41 044
Feb. 24, 2004  (DE) ...................... 10 2004 009 452

(51) Int. Cl.
*A61N 1/36* (2006.01)
(52) U.S. Cl. ................................. 607/48; 607/2; 607/50
(58) Field of Classification Search .................... 607/2, 607/48, 115, 116
See application file for complete search history.

(56) References Cited

U.S. PATENT DOCUMENTS

| 4,232,679 | A | * | 11/1980 | Schulman .................... 607/33 |
| 4,406,287 | A |   | 9/1983  | Nappholz et al. |
| 4,773,401 | A |   | 9/1988  | Citak et al. |
| 5,016,632 | A |   | 5/1991  | Hoegnelid et al. |
| 5,271,396 | A | * | 12/1993 | Franberg et al. ............. 607/17 |
| 5,292,341 | A |   | 3/1994  | Snell |
| 2003/0083703 | A1 |   | 5/2003 | Zhu et al. |

FOREIGN PATENT DOCUMENTS

DE        101 52 741 A1      2/2003

* cited by examiner

*Primary Examiner*—Carl H. Layno
*Assistant Examiner*—Brian T Gedeon
(74) *Attorney, Agent, or Firm*—Henry M. Feiereisen; Ursula B. Day

(57) ABSTRACT

The invention relates to a device for muscle stimulation, said device comprising a pulse generator unit (9) for producing and sending an electrical stimulation pulse; a control unit (10) for controlling the pulse generator unit (9) in order to adjust the amplitude and the frequency of the stimulation pulses and to cause the transmission of stimulation pulses to a muscle to be stimulated; a detection unit (11) for detecting the instantaneous, spontaneous or stimulated cardiac rhythm of the carrier of the device; a housing (12) receiving the pulse generator unit (9), the control unit (10), and the detection unit (11); a counting unit (13) and a memory unit (14) for counting and storing the number of stimulation pulses emitted within a definable time interval; and a determination unit (15) for determining the arithmetic average of the stimulation frequency within the definable time interval.

24 Claims, 2 Drawing Sheets

DEVICE FOR MUSCLE STIMULATION

BACKGROUND OF THE INVENTION

The invention relates to a device for muscle stimulation.

Muscle-driven heart assist systems (for example cardio myoplasty, aorta myoplasty, skeletal muscle ventricle, biomechanical hearts) are nowadays already employed in clinical settings, for example experimentally as assist or replacement therapy of heart transplantation and treatment of a terminal heart insufficiency. These muscle assist systems can operate both in parallel and in series with the diseased heart. The systems are intended to relieve (reduce the cardiac wall tension, relieve pressure, relieve volume, relieve post-stress) and also to assist the circulation, i.e., increase the average pressure of the arterial blood pressure and/or to increase the pump volume. Independent of the configuration of the heart assist system, a muscle pacemaker is required for deliberate stimulation of a muscle contraction, which transmits to the muscle to be assisted an electrical stimulation pattern in synchronism with the heart beat via stimulation electrodes. A stimulation pattern consists of a sum of individual pulses which can be characterized by their stimulation voltage, the pulse width and the spacing between two pulses. By a meaningful combination of several individual pulses to a group of individual pulses with a subsequent pause, a stimulation burst is created which can be used cyclically contract and relax the muscle tissue. In addition to the aforedescribed parameters, the number of stimulation pulses per burst and the frequency with which a stimulation burst is applied can be used to describe a stimulation pattern. An additional parameter is the placement of the stimulation burst within the heart cycle, which can be defined by a delay time.

Experiments on large animals have shown that a continuous and frequent application of stimulation burst causes a fiber transformation of the stimulated muscle tissue, with the generated muscle fibers being substantially free of fatigue, but weak and slow. It has been observed that the muscle fiber cross-sections significantly decrease when stimulation bursts are applied continuously and frequently. The muscle tissue, which is here mainly represented by the type-I muscle fibers, is barely suitable to perform the pumping benefiting the circulation. However, experimental tests have shown that before the stimulated muscle fibers are transformed into type-I muscle fibers, they are transformed into an intermediate, already fatigue-free form, which still includes strong type-IIa muscle fibers. This quick and strong muscle tissue, which is dominated by type-IIa muscle fibers, is only preserved if the number of applied stimulation pulses per time interval remains below an upper limit value. Stimulation above this upper limit causes the type-IIa muscle fibers to transformation into type-I muscle fibers, accompanied by a loss in muscle strength and quickness.

Conventional muscle pacemaker systems are capable of supplying predefined or computed stimulation bursts synchronously with and triggered by the heart rhythm, wherein the ratio of muscle contraction to heart contraction is adjustable. This ratio can be predefined as a function of the heart rate. For example, if a high heart rate persists over an extended period of time, then the same high number of stimulation pulses is supplied by the muscle pacemaker. The utilization of the muscular heart assist system is then exceedingly high, so that most of the muscle fibers are transformed into weak and slow type-I muscle fibers. Muscular-driven heart assist systems then lose their effectiveness, so that the diseased heart can no longer be effectively relieved. The support of the circulatory system deteriorates with increased utilization, so that the heart rate of the patient may increase further to compensate this effect. This can cause the supported muscle to completely degenerate.

DE 101 52 741 A1 discloses a heart therapy device, in particular an implantable defibrillator, heart pacemaker or combined heart pacemaker-defibrillator, with an evaluation and control unit for evaluating a measured heart rate. The evaluation and control unit includes a memory with three ranges for storing a first, a second, and a third range of values of comparative heart rates. The adjacent ranges are organized by increasing values of the heart rate. The evaluation and control unit further includes a heart rate discriminator for associating a measured heart rate with the first, second or third range of values, and a stability evaluation unit for evaluating the stability or constancy of the heart rate over a predetermined time interval, when a heart rate in the second range of values is detected. When a heart rate in the second range of values is detected, one of two different therapy control signals is supplied, depending on the stability of the heart rate. The stability criterion is used to distinguish between "rapid" tachycardia ("flutter") and fibrillations with a-still-relatively low frequency. U.S. Pat. No. 4,406,287 also discloses a pacemaker. This device is intended to terminate tachycardia, wherein different pulse numbers/pulse rates can be employed. If tachycardia is not terminated after applying a first combination of a certain number of pulses and a certain pulse rate, then a second phase is applied with a changed combination of pulse number and pulse rate. The last successful combination of pulse number and pulse rate is then stored as a starting value for terminating the next tachycardia. With this approach, the probability for terminating a tachycardia can be enhanced.

U.S. published patent application 2003/0083703 A1 discloses a method and a device for providing an anti-tachycardia pulse pattern. This device is also capable of determining if a pulse pattern has terminated a tachycardia and if a change in the pulse pattern is indicated.

SUMMARY OF THE INVENTION

It is therefore an object of the invention to provide a muscle stimulator which makes it possible to preserve type-IIa muscle fibers and, more particularly, to provide an effective heart muscle assist system which operates when needed. The muscle stimulator should also be capable of inducing, through suitable electrical stimulation, the formation of new blood vessels and capillaries for optimally supplying the muscle tissue with blood (neo-vascularization).

The object can be solved with a muscle stimulator which includes a pulse generator unit for generating and transmitting an electric stimulation pulse, a control unit for controlling the pulse generator unit (9) for setting amplitude and frequency of the stimulation pulses and for causing stimulation pulses to be applied to a muscle to be stimulated, a detection unit for detecting the instantaneous, spontaneous or stimulated heart rhythm of the wearer of the device, a housing for receiving the pulse generator unit, the control unit and the detection unit, wherein a counting unit and a memory unit for counting and storing the number of stimulation pulses transmitted during a defined time interval, and a determination unit for determining an arithmetically averaged (mean) stimulation frequency within the definable time interval are provided, wherein the mean stimulation frequency is computed as the quotient of the stimulation pulses transmitted during the defined time interval and stored in the memory unit and the defined time interval in which the stimulation pulses are counted and stored.

The subject matter of the present invention is directed to a muscle stimulator with a pulse generator unit for producing and transmitting an electrical stimulation pulse, as well as a control unit for controlling the pulse generator unit. The amplitude, i.e., the stimulation voltage, the frequency, the temporal distribution of the stimulation pulses, the type and frequency of the support modes and the delay time relative to the R-spike, the day/night rhythm and the phase position of the stimulation pulse can be adjusted with the control unit. The stimulation pulses are transmitted from the control unit via wiring means to one or more muscles to be stimulated. The muscle stimulator according to the invention also includes a determination unit for determining the instantaneous, spontaneous or the stimulated heart rhythm of the wearer of the muscle stimulator. The determination unit measures the R-spike, which is used as a basis for triggering the stimulation pulse and for calculating the time delay between the R-spike of the heart rhythm and the stimulation burst. The pulse generator unit, the control unit, and the detection unit are housed in a common housing, which can be carried external to the patient's body or can be implanted in the patient's body.

A counting unit and a memory unit for counting and storing the number of stimulation pulses transmitted within a definable time interval are also provided, as is a determination unit for determining a mean stimulation frequency within the definable time interval.

The mean stimulation frequency according to the invention is the quotient formed of the stimulation pulses, which are supplied within a definable time interval and stored by the memory unit, and the defined time interval, during which the stimulation pulses are counted and stored (detection time interval/observation time interval). This represents an arithmetically averaged (mean) stimulation frequency, whereby in the following the term "mean stimulation frequency" will be used interchangeably with "arithmetically averaged stimulation frequency."

The counting unit and/or the memory unit and/or the determination unit are not necessarily housed inside the aforementioned housing, but may also be housed in a separate housing, in particular a housing carried external to the patient's body.

To prevent the stimulated muscles from being overstimulated and the stimulated muscle fibers from being transformed into a weak, slow and hence ineffective type-I muscle tissue, the stimulation pulses transmitted within a definable time interval must be counted and evaluated. This task is performed by the counting unit in cooperation with the storage unit and a monitoring unit. The mean stimulation frequency is a measure for the frequency with which the muscles are stimulated during a certain time interval. To prevent muscle damage, the mean stimulation frequency must not continuously exceed an individually determined limit value.

Each transmitted stimulation pulse is counted and computed over an extended observation time to yield a mean stimulation frequency. A longer observation time according to the invention has a duration of at least 30 minutes, in particular one hour or several hours. Advantageously, observation times are 12 or 24 hours. The mean stimulation frequency must be determined individually for each patient and must not exceed a maximum value of the 0.2 to 2 pulses per second (Hz), in particular 0.7 to 1 Hz, so as to prevent overexertion of the muscle and a medium-term muscle destruction. The mean stimulation frequency should therefore be evaluated so as to arrive at the desired muscle transformation and preservation effect, and to control the transmission of stimulation pulses depending on the outcome of the evaluation. For this purpose, a continuously operating evaluation unit for observing the limit values for the mean stimulation frequency is provided, wherein the limit values can be individually set in a range of 0.2 stimulation pulses per second to 2 stimulation pulses per second. Pulse conservation means, also referred to as pulse saving means, are provided for adapting and, more particularly, reducing the mean stimulation frequency as a function of the measured mean stimulation frequency and the defined desired values of the evaluation unit. The pulse conservation means include a computing unit for computing a modified stimulation pattern according to an equation which depends on the mean stimulation frequency. In addition, a memory module for storing the temporal course of the number of supplied stimulation pulses can be provided, as well as means for program-controlled transmission of the mean stimulation frequency from the determination unit to the computing unit. Moreover, an analysis unit can be provided for determining when and how often certain limit values of the heart rate and/or of the mean stimulation frequency are exceeded or underrun.

The counting unit and the memory unit can be housed in the aforedescribed housing. The determination unit and/or the pulse conservation means can also be integrated in the housing. Optionally, the memory module and/or the analysis unit can also be integrated in the housing that houses the control unit. The housing can be implanted in the body of the wearer of the device of the invention. An energy storage device which can preferably be recharged transcutaneously can also be associated with the housing. This increases the operating time of the implanted part of the device.

Within the context of the invention, the counting unit and/or the memory unit and/or the determination unit and/or the pulse conservation means and/or the memory module and/or the analysis unit can form a part of a stationary monitoring unit and/or a monitoring unit worn by the wearer of the device external to the body. The mean stimulation frequency and/or a range of values in which the mean stimulation frequency falls, can be optically and/or acoustically and/or haptically displayed on the monitoring unit. The monitoring unit can optionally include programming unit for generating a programming signal and a transmission unit for transmitting the programming signal to a send and receive unit in the housing which houses the control unit. The monitoring unit can also include means for sending and receiving position data. The monitoring unit can further includes means for sending and receiving wireless signals for the purpose of transmitting patient-physiological data to a display and evaluation unit of a receiver It is another object of the invention to provide a combination of specially developed electronic devices for muscular heart assist systems, in particular for muscular blood pumps, capable of generating and maintaining type-IIa muscle fibers. The invention also relates to a myo-stimulator which can be programmed to preoperatively generate through percutaneous stimulation type-IIa muscle fibers showing less fatigue. This device can include an implantable myo-stimulator and a monitoring unit which effectively contracts the muscle with type-IIa muscle fibers, prevents conversion to type-I muscle fibers, and also prevents destruction of muscle from excessive stress. The monitoring unit associated with this implantable myo-stimulator can be used as a programming unit as well as a measurement and display device. The monitoring unit can transmit information either wireless or by a wired connection from the bio-stimulator to the patient or to the attending physician. Additional functions can be incorporated in this device, such as transmitting the ECG of the patient and/or a patient location system for emergencies. This device can also implement to a limited extent the aforedescribed functions in myo-stimulators of other manufacturers.

BRIEF DESCRIPTION OF THE DRAWING

The invention will now be described with reference to schematically illustrated embodiments.

DETAILED DESCRIPTION OF PREFERRED EMBODIMENTS

Figure 1:
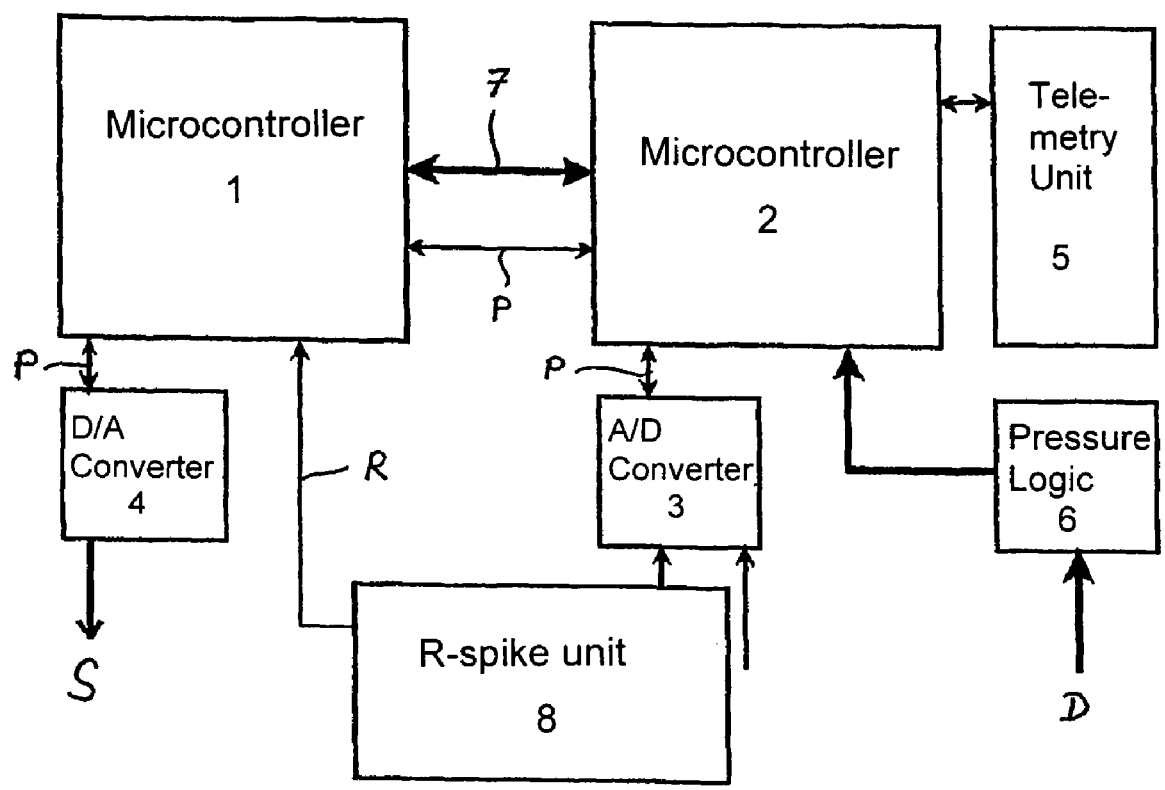
FIG. 1 shows schematically the interconnections between different physical elements of an apparatus of the invention.

FIG. 1 depicts an embodiment with two microcontrollers 1, 2 as programmable components. The microcontrollers have a large number of programmable ports, a high processing speed with moderate power consumption, and a flash memory with in-system programmability (ISP). Additional components of the muscle pacemaker are a 12 bit analog-to-digital converter (A/D converter) 3, a 12 bit digital-to-analog converter (D/A converter) 4, several operational amplifiers, and a telemetry unit 5. Long-life batteries, preferably lithium ion batteries, supply power.

The digital portion of the muscle pacemaker is essentially divided into two logically separate regions, which are each operated with a dedicated microcontroller 1, 2 as programmable components. The first region, controlled by the microcontrollers 1, is used to generate, amplify and distribute the stimulation pulses S (max. 40 mA) to four muscle electrodes and two cardiac electrodes. The second region, controlled by the microcontroller 2, is used for monitoring the patient, for capturing and storing measurement data, e.g., pressure data D, which are processed in a pressure logic 6 and then supplied to the microcontroller 2 which operates as a measurement unit, as well as for telemetric communication with the environment. The two logical regions are connected with each other via a multi-purpose connection in the form of a serial interface 7. The two microcontrollers 1, 2 are programmed, for example, in the programming language "C". The actual software of the microcontrollers 1, 2 can be different, depending on their specific function.

The functions of the aforementioned logically separate regions will now be described in more detail.

Region 1:

Triggering From the Heart Action:

To suitably place a stimulation pulse within a heart cycle, the microcontroller 1 receives synchronously with each heart action a trigger signal from a filter circuit (R-spike unit) 8, which includes 8 cascaded operational amplifiers OPV. The first four OPVs amplify the receives ECG signal from approximately 1-10 mV to 2-3 V and filter out interference frequencies of 50 Hz and 60 Hz. The additional 4 stages are used to extract the R-spike and to generate a Schmitt-trigger signal. This trigger signal is detected by the microcontroller 1, and the time interval from the preceding trigger signal is determined. If the determined time interval is normal when compared to the last 10 trigger intervals, a stable sinusoidal rhythm of the heart is assumed and the heart rate is determined from the spacing of the trigger signals R. Each of the arrows having the reference symbol P indicates serial high-speed links.

Assist Modes

Different ratios of the muscle contraction to heart contraction are desirable depending on the heart rate. The adjustable range is between 1:1, i.e., each heart action is supported by a muscle action, and 1:255, i.e., the muscle contracts only after 255 heart actions. Up to 5 different support modes can be defined depending on the heart rate.

Day-Night Rhythm and/or Activity-Rest Rhythm

Day times and night times and, independently thereof, activity times and rest times can be defined for the muscle pacemaker, whereby the muscle pacemaker switches between pulse patterns having high activity and pulse patterns having low activity or no activity. The switch between day and night rhythms and/or activity-rest rhythms can be time-dependent, event-controlled, or manually through a controller of the patient.

Time Sequence Before a Muscle Stimulation

When a heart trigger signal R is received and the signal is deemed to be regular, a counter performs an addition until a heart pulse occurs which requires assistance. Thereafter, a second counter is activated which introduces a certain time delay before the stimulation pattern is generated (R-spike delay, R-delay).

Time Sequence During a Muscle Stimulation

At the end of the R-spike delay time (R-delay), the D/A converter 4 and an operational amplifier circuit (OPV) generate the stimulation pattern pulse-by-pulse, depending on the preset, with the variables: amplitude, pulse width, pulse phase (positive, negative, biphasic) and inter-pulse spacing, and supply the stimulation pattern to defined stimulation electrodes.

Quantifying the Stimulation Pulse

Each supplied stimulation pulse is counted and a mean stimulation frequency is computed over an observation time interval of, for example, 24 hours. The mean stimulation frequency must be determined individually for each patient and must not exceed a maximum value of approximately 0.2 Hz to 2 Hz, in particular 0.7 to 1 Hz, so as to prevent overstraining the muscle and medium-term muscle destruction.

Output of the Mean Stimulation Frequency

Providing an output of the mean stimulation frequency represents an important and novel feedback mechanisms for the wearer of the muscle pacemaker and for the attending physician, so that overstraining the muscle can be identified early and countermeasures can be taken to prevent potential destruction of the muscle. The microcontroller transmits the mean stimulation frequency via a radio link in regular intervals, which can be adjusted by the physician, which is received by a portable patient monitor and is indicated to the patient, for example, displayed. If the mean stimulation frequency is in a critical range, the microcontroller transmits the data immediately; the patient monitor then signals an overload alert. The patient can then reduce the heart rate and the frequency of assist of the heart muscle by reducing his/her bodily activity.

Pulse Conservation Mode

If the mean stimulation frequency is in a range close to the upper limit, then the automatic pulse conservation mode can be operative, if this mode was activated by the physician and/or by the wearer of the implant. In this mode, the stimulation pulses are distributed within the stimulation burst at a low activity, so that initially a sufficient number of pulses for a muscle contraction is generated, whereas during the further course of the stimulation one to two pulses are cut out by stretching, i.e., reducing the stimulation frequency. For safety reasons, this mechanism is not operative in phases of high activity.

Region 2:

Patient Monitoring and Communication Unit

The second region of the muscle pacemaker is used for monitoring the patient, for measuring and storing the measurement data, and for telemetric communication with the environment.

Real-Time Patient Monitoring

Real-time patient monitoring allows the attending physician to gain an overview over the instantaneous physiological data, such as ECG, EMG, and blood pressure. After activation of the measurement module, the data from the implanted device are measured via the respective electrodes (ECG and heart rhythm; heart sensing electrodes; EMG: stimulation electrodes) and sensors (absolute pressure sensor), digitized and transmitted in compressed form to the outside via a radio link. The data are graphically displayed on the receiving monitoring unit (patient monitor) and logged. The patient monitor can include an interface with a telecommunication path, for example a telephone line, for remote diagnostic monitoring of the patient.

Measuring and Storing of "Long-Term" Physiological Data

The monitoring unit of the muscle pacemaker measures cyclically (adjustable from 1 minute to 1 hour) the heart rate and the systolic and diastolic blood pressure. These data are stored internally in the pacemaker in form of a table, and a trend analysis is performed. This stored table values are transferred routinely, once a day, to the monitoring unit which transmits the data to the attending physician, for example via a telephone dial-up connection. However, if the trend analysis indicates a life-threatening risk for the patient, then the result of the analysis is immediately telemetrically transferred to the monitoring unit. If limit values defined by the physician are exceeded, then the monitoring unit informs the attending physician or an emergency center and transmits, in particular, via a wireless radio link (UMTS/GSM) both the patient data and the GPS position of the patient.

Programmability of the Muscle Pacemaker

The implanted device must be capable of responding to external inquiries for changing the existing stimulation pattern and for activating/deactivating the various operating modes. For this reason, the telemetry component and the microcontroller 2 are periodically placed in a receive mode (adjustable from seconds to several hours).

The following parameters of the stimulation pattern can be reprogrammed:
  Stimulation voltage,
  Stimulation phase,
  Temporal distribution of the stimulation pulses,
  Type and frequency of the assist modes,
  Delay time relative to the R-spike,
  Duration of the day and night rhythm, or of the activity and rest rhythm,
  Electrode position.

The following operating modes can be activated and/or deactivated:
  Day and night rhythm, or the activity and rest rhythm,
  Pulse conservation mode,
  Real-time capture of measurement data,
  Pacemaker diagnostic program,
  Impedance measurement of the stimulation electrodes,
  Battery voltage measurement.

The patient monitor (monitoring unit) is a battery-operated system that can be worn by a patient.

It can be used for
  Self-check by the patient to attain the mean stimulation frequency in a range from 0.2 Hz to 2 Hz, in particular 0.7 to 1 Hz, over for example 24 hours, whereby an illuminated color display (green, yellow, red) signals the mean stimulation frequency, which is periodically updated;
  Tele-monitoring the patient by the attending physician, wherein the physiological real-time and long-term data measured by the implant are telemetrically received, logged and routed onward. The data can be routed onward either via the integrated telephone modem or via a radio link in a wireless network, for example a UMTS/GSM network;
  Determining the position of the patient in emergency situations via an integrated GPS receiver;
  A programming unit to allow the patient him-/herself to set fundamental stimulation parameters and operating modes.

The patient monitor includes a microcontroller, a telemetry module, a standard GPS receiver, a standard modem and a UMTS/GSM module.

The patient monitor is provided with a graphic display and illumination means, in particular an LED display, for visualizing the mean stimulation frequency and status messages of the system. The data can be entered under menu-control via keys or alternatively by using a stylus.

Figure 2:
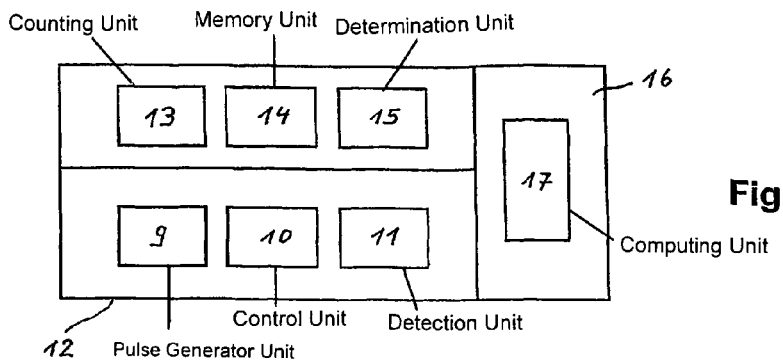
FIG. 2 is a diagram of the functional elements of a first embodiment of a device for muscle stimulation.

FIG. 2 shows a device for muscle stimulation with a pulse generator unit 9 for generating and sending an electric stimulation pulse, a control unit 10 for controlling the pulse generator unit 9, for setting the amplitude and frequency of the stimulation pulses, and for causing transmission of stimulation pulses to a muscle requiring stimulation. A detection unit 11 for measuring the instantaneous, spontaneous, or stimulated heart rhythm of the wearer of the device is also provided. The basic components of the device of the invention for muscle stimulation are housed in a common housing 12. The housing also includes a counting unit 13 and a memory unit 14 for counting and storing the number of stimulation pulses supplied within a definable time interval. An additional determination unit 15 is used to determine a mean stimulation frequency within a definable time interval. The housing 12 also includes a pulse conservation means 16 with a computing unit 17. The computing unit 17 is used to compute a stimulation pattern according to an equation which determines the stimulation pattern as a function of the mean stimulation frequency.

Figure 3:
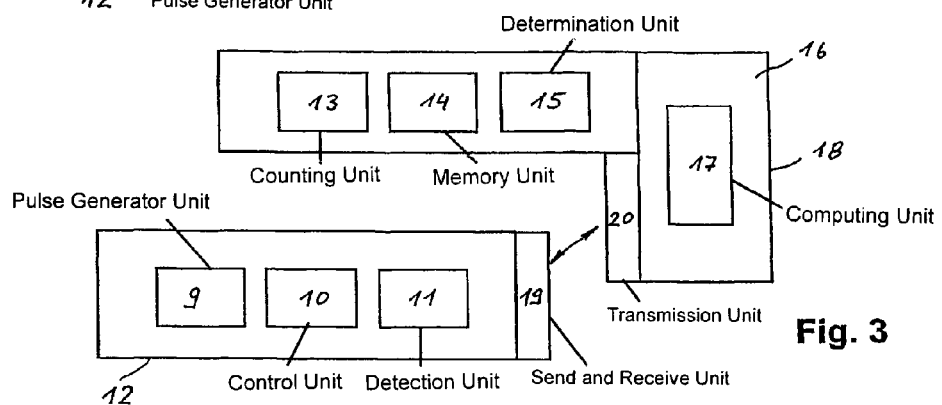
FIG. 3 shows a modification of the embodiment of FIG. 1.

Unlike the embodiment depicted in FIG. 2, the embodiment of FIG. 3 includes two spatially separated housings 12, 18. The housing 12 with the pulse generator unit 9, the control unit 10 and the detection unit 11, as well as a send and receive unit 19 for communicating with the component in the other housing 18, can be implanted in the patient's body. In the depicted exemplary embodiment, the counting unit 13, the memory unit 14, the determination unit 15 and the pulse conservation means 16 are spatially separate from the implanted housing. The respective housings 12, 18 can communicate via a wireless communication link provided by the send and receive unit 19 and the transmission device 20 in the respective housings.

Figure 4:
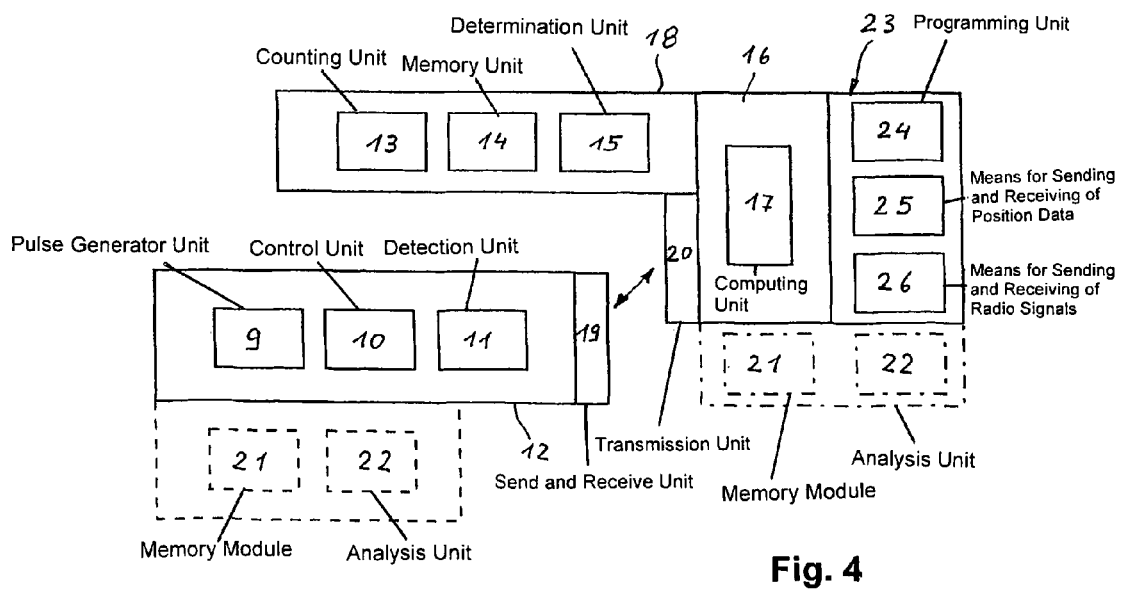
FIG. 4 shows another variation of the device for muscle stimulation with additional functional elements.

The embodiment of FIG. 4 has additional components in the housing 18 located external to the patient's body. The housing 18 further includes a memory module 21 for storing the temporal course of the number of applied stimulation pulses, and an analysis unit 22 for determining how often and when the heart rate and/or the mean stimulation frequency exceeded or fell below certain limit values. These components are shown in FIG. 4 with dash-dotted lines and can optionally also be included directly in the implanted housing 12. A broken line in the diagram of FIG. 4 is meant to indicate that these components are located adjacent to the housing 12. Because in the exemplary embodiment of FIG. 4 major functional components of the device of the invention are arranged in the housing 18 external to the patient's body, this assembly can also function as the monitoring unit 23. A programming unit 24 is provided on the monitoring unit 23, with programmed control commands being supplied via the transmission unit 20 and the send and receive unit 19 to the control unit 10 in the housing 12. In the depicted exemplary embodiment, the monitoring unit 23 further includes means 25 for sending and receiving position data, as well as means 26 for sending and receiving radio signals to transmit patient-physiological data to a display and evaluation unit of a receiver. The monitoring unit 23 includes optical and/or acoustic and/or haptic display means for indicating the mean stimulation frequency.

What is claimed is:

1. A device for stimulating a muscle contraction of a muscular-driven heart assist system which operates in parallel or in series with a diseased heart, comprising:
   a pulse generator unit for generating and supplying electric stimulation pulses to a muscle of the muscular-driven heart assist system;
   a control unit for controlling the pulse generator unit for setting an amplitude and a frequency of the stimulation pulses and for causing the stimulation pulses to be applied to the muscle of the muscular-driven heart assist system to be stimulated;
   a detection unit for detecting an instantaneous, spontaneous or stimulated heart rhythm of a wearer of the device;
   a housing receiving the pulse generator unit, the control unit and the detection unit;
   a memory module for storing a temporal course of the number of supplied stimulation pulses within a defined time interval;
   a counting unit and a memory unit for counting and storing a number of stimulation pulses supplied during the defined time interval, wherein the stimulation pulses are grouped into variable stimulation bursts;
   a determination unit for determining an arithmetically averaged (mean) stimulation frequency within the defined time interval, with the mean stimulation frequency being computed as the quotient of the number of stimulation pulses of the variable stimulation bursts supplied during the defined time interval and stored in the memory unit and the defined time interval in which the stimulation pulses are counted and stored;
   a continuously operating evaluation unit for ascertaining that the mean stimulation frequency stays within preset limit values, wherein the limit values of the mean stimulation frequency can be preset in a range between 0.2 stimulation pulses per second and a maximum of 2 stimulation pulses per second;
   pulse conservation means for reducing the mean stimulation frequency depending on the limit values preset in the evaluation unit, wherein the pulse conservation means comprise a computing unit configured to compute a stimulation pattern according to an equation which determines the stimulation pattern as a function of the mean stimulation frequency and varies the number of stimulation pulses during a stimulation burst to generate and maintain type-IIa muscle fibers and to revent their conversion to type-I muscle fibers; and
   a monitoring unit worn by the wearer of the device external to the body for displaying the mean stimulation frequency and for self-control of the patient.

2. The device of claim 1, further comprising means for program-controlled transmission of the mean stimulation frequency from the determination unit to the evaluation unit.

3. The device of claim 1, further comprising an analysis unit for determining how often and when certain limit values of the heart rate and/or of the mean stimulation frequency are exceeded or underrun.

4. The device of claim 1, wherein the counting unit and the memory unit are received in the housing.

5. The device of claim 1, wherein the determination unit and/or the pulse conservation means are integrated in the housing which receives the control unit.

6. The device of to claim 3, wherein the memory module and/or the analysis unit are integrated in the housing which receives the control unit.

7. The device of claim 1, wherein the monitoring unit comprises a programming unit for generating a programming signal, and a transmission unit for transmitting the programming signal to a send and receive unit located in the housing which receives the control unit.

8. The device of claim 1, wherein at least one of the counting unit, the memory unit, the determination unit, the pulse conservation means, the memory module and the analysis unit are a part of a stationary monitoring unit or of the monitoring unit worn by the wearer of the device external to the body.

9. The device of claim 1, wherein the mean stimulation frequency, or an order of magnitude of the mean stimulation frequency, is displayed on the monitoring unit by optical, acoustic or haptic means, or a combination thereof.

10. The device of claim 1, wherein the monitoring unit includes means for sending and receiving position data.

11. The device of claim 10, wherein the monitoring unit includes means for sending and receiving wireless signals for transmitting patient-physiological data to a display and evaluation unit of a remote receiver.

12. The device of claim 1, wherein the pulse generator unit transmits biphasic stimulation pulses.

13. The device of claim 1, further comprising a transcutaneously chargeable energy storage device received in the housing.

14. The device of claim 1, wherein the defined time interval is at least 30 minutes.

15. The device of claim 1, wherein the defined time interval is at least 12 hours.

16. The device of claim 1, wherein the defined time interval is at least 24 hours.

17. The device of claim 1, wherein the amplitude of the stimulation pulses within a stimulation burst is variable.

18. The device of claim 1, wherein a pulse width of the stimulation pulses within a stimulation burst is variable.

19. The device of claim 1, wherein a temporal spacing between two stimulation pulses within a stimulation burst is variable.

20. A method for generating and maintaining type-IIa muscle fibers and prevent their conversion to type-I muscle fibers in a muscular-driven heart assist system which operates in parallel or in series with a diseased heart, comprising the steps of:

detecting an instantaneous, spontaneous or stimulated heart rhythm of the diseased heart;

setting a limit value for an mean stimulation frequency for stimulation pulses applied to the heart assist system between a minimum of 0.2 stimulation pulses per second and a maximum of 2 stimulation pulses per second;

setting a pattern of the stimulation pulses based on the heart rhythm, with the stimulation pulses being grouped into variable stimulation bursts;

determining the mean stimulation frequency from a total number of applied stimulation pulses during a defined time interval; and if the mean stimulation frequency exceeds the upper limit value, decreasing the number of the stimulation pulses in the stimulation bursts so as to reduce the mean stimulation frequency below the limit value and to generate and maintain the type-IIa muscle fibers.

21. The method of claim 20, wherein the limit value is between a minimum of 0.7 stimulation pulses per second and a maximum of 1 stimulation pulse per second.

22. The method of claim 20, wherein the defined time interval is at least 1 hour.

23. The method of claim 20, wherein the defined time interval is between 12 hours and 24 hours.

24. The method of claim 20, and further displaying the mean stimulation frequency and displaying or transmitting, or both, an alarm when the mean stimulation frequency exceeds the upper limit value.

* * * * *